(12) United States Patent
Cox et al.

(10) Patent No.: US 8,685,018 B2
(45) Date of Patent: Apr. 1, 2014

(54) ELECTROSURGICAL WAND AND RELATED METHOD AND SYSTEM

(75) Inventors: David A. Cox, Austin, TX (US);
Johnson E. Goode, Austin, TX (US);
Philip M. Tetzlaff, Austin, TX (US);
Jean Woloszko, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 728 days.

(21) Appl. No.: 12/905,386

(22) Filed: Oct. 15, 2010

(65) Prior Publication Data

US 2012/0095453 A1    Apr. 19, 2012

(51) Int. Cl.
*A61B 18/14* (2006.01)

(52) U.S. Cl.
USPC .......................................................... 606/41

(58) Field of Classification Search
USPC ................................. 606/27, 34, 41
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |
| 2,611,365 A | 9/1952 | Rubens | 606/42 |
| 3,434,476 A | 3/1969 | Shaw et al. | 606/22 |
| 3,633,425 A | 1/1972 | Sanford | 73/356 |
| 3,707,149 A | 12/1972 | Hao et al. | 128/303.14 |
| 3,718,617 A | 2/1973 | Royal | 260/30.4 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,963,030 A | 6/1976 | Newton | 606/40 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |

(Continued)

FOREIGN PATENT DOCUMENTS

| | | | | |
|---|---|---|---|---|
| DE | 3119735 | | 1/1983 | A61B 17/39 |
| DE | 3930451 A1 | | 3/1991 | A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Michael Peffley
*Assistant Examiner* — Daniel Fowler
(74) *Attorney, Agent, or Firm* — Matthew Scheele; Brian E. Szymczak

(57) ABSTRACT

An electrosurgical wand. At least some of the illustrative embodiments are electrosurgical wands including an elongate housing that defines a handle end and a distal end, a first discharge aperture on the distal end of the elongate housing, a first active electrode of conductive material disposed on the distal end of the elongate housing, a first return electrode of conductive material disposed within the first fluid conduit, and an aspiration aperture on the distal end of the elongate housing fluidly coupled to a second fluid conduit.

35 Claims, 8 Drawing Sheets

(56) References Cited

U.S. PATENT DOCUMENTS

| | | | |
|---|---|---|---|
| 4,074,718 A | 2/1978 | Morrison, Jr. | 128/303 |
| 4,092,986 A | 6/1978 | Schneiderman | 128/303 |
| D249,549 S | 9/1978 | Pike | D24/144 |
| 4,114,623 A | 9/1978 | Meinke et al. | 606/39 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,301,801 A | 11/1981 | Schneiderman | 606/38 |
| 4,326,529 A | 4/1982 | Doss et al. | 128/303 |
| 4,346,715 A | 8/1982 | Gammell | 607/99 |
| 4,363,324 A | 12/1982 | Kusserow | 607/64 |
| 4,378,801 A | 4/1983 | Oosten | 606/37 |
| 4,381,007 A | 4/1983 | Doss | 128/303 |
| 4,418,692 A | 12/1983 | Guay | 606/42 |
| 4,474,179 A | 10/1984 | Koch | 606/40 |
| 4,476,862 A | 10/1984 | Pao | 128/303 |
| 4,509,532 A | 4/1985 | DeVries | 128/736 |
| 4,520,818 A | 6/1985 | Mickiewicz | 606/40 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,750,902 A | 6/1988 | Wuchinich et al. | 604/22 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,846,179 A | 7/1989 | O'Connor | 607/72 |
| 4,860,752 A | 8/1989 | Turner | 607/102 |
| 4,898,169 A | 2/1990 | Norman et al. | 606/42 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,026,387 A | 6/1991 | Thomas | 606/169 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins et al. | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,174,304 A | 12/1992 | Latina et al. | 607/141 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,334,183 A | 8/1994 | Wuchinich | 606/46 |
| 5,334,193 A | 8/1994 | Nardella | 606/41 |
| 5,336,172 A | 8/1994 | Bales et al. | 604/27 |
| 5,336,220 A | 8/1994 | Ryan et al. | 604/22 |
| 5,342,357 A | 8/1994 | Nardella | 606/40 |
| 5,348,554 A | 9/1994 | Imran et al. | 606/41 |
| 5,354,291 A | 10/1994 | Bales et al. | 604/35 |
| 5,366,443 A | 11/1994 | Eggers et al. | 252/511 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,874 A | 1/1995 | Jackson et al. | 606/1 |
| 5,383,876 A | 1/1995 | Nardella | 606/49 |
| 5,383,917 E | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |

(56) References Cited

U.S. PATENT DOCUMENTS

| | | | |
|---|---|---|---|
| 5,505,730 A | 4/1996 | Edwards | 606/41 |
| 5,507,743 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,609,573 A | 3/1997 | Sandock | 604/22 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,700,262 A | 12/1997 | Acosta et al. | 606/48 |
| 5,715,817 A | 2/1998 | Steven-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A | 12/2000 | Meyer-ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 * | 4/2002 | Sharkey et al. | 606/41 |
| 6,379,351 B1 | 4/2002 | Thapliyal et al. | 606/41 |
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,425,912 B1 | 7/2002 | Knowlton | 607/101 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,500,173 B2 | 12/2002 | Underwood et al. | 606/32 |
| 6,514,248 B1 | 2/2003 | Eggers et al. | 606/41 |

(56) References Cited

U.S. PATENT DOCUMENTS

| | | | |
|---|---|---|---|
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,640,128 B2 | 10/2003 | Vilsmeier et al. | 600/427 |
| 6,656,177 B2 | 12/2003 | Truckai et al. | 606/51 |
| 6,663,554 B2 | 12/2003 | Babaev | 600/2 |
| 6,663,627 B2 | 12/2003 | Francischelli et al. | 606/41 |
| 6,702,810 B2 | 3/2004 | McClurken et al. | 606/34 |
| 6,730,080 B2 | 5/2004 | Harano et al. | 606/38 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| D493,530 S | 7/2004 | Reschke | D24/144 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,780,184 B2 | 8/2004 | Tanrisever | 606/45 |
| 6,802,842 B2 | 10/2004 | Ellman et al. | 606/45 |
| 6,830,558 B2 | 12/2004 | Flaherty et al. | 604/67 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,864,686 B2 | 3/2005 | Novak et al. | 324/419 |
| 6,866,671 B2 | 3/2005 | Tierney et al. | 606/130 |
| 6,872,183 B2 | 3/2005 | Sampson et al. | 600/561 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,921,398 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,953,461 B2 | 10/2005 | McClurken et al. | 606/51 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 606/41 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,223,265 B2 | 5/2007 | Keppel | 606/41 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,271,363 B2 | 9/2007 | Lee et al. | 219/121.43 |
| 7,276,061 B2 | 10/2007 | Schaer et al. | 607/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,527,624 B2 | 5/2009 | Dubnack et al. | 606/41 |
| 7,572,251 B1 | 8/2009 | Davison et al. | 604/500 |
| 7,632,267 B2 | 12/2009 | Dahla | 606/41 |
| 7,678,069 B1 | 3/2010 | Baker et al. | 604/22 |
| 7,691,101 B2 | 4/2010 | Davison et al. | 606/41 |
| 7,699,830 B2 | 4/2010 | Martin | 604/540 |
| 7,704,249 B2 | 4/2010 | Woloszko et al. | 606/48 |
| 7,708,733 B2 | 5/2010 | Sanders et al. | 606/41 |
| 7,722,601 B2 | 5/2010 | Wham et al. | 606/34 |
| 7,785,322 B2 | 8/2010 | Penny et al. | 606/34 |
| 7,824,398 B2 | 11/2010 | Woloszko et al. | 606/32 |
| 7,862,560 B2 | 1/2011 | Marion | 606/34 |
| 7,985,072 B2 | 7/2011 | Belikov et al. | 433/215 |
| D658,760 S | 5/2012 | Cox et al. | D24/144 |
| 8,192,424 B2 | 6/2012 | Woloszko | 606/40 |
| 8,257,350 B2 | 9/2012 | Marion | 606/38 |
| 8,303,583 B2 | 11/2012 | Hosier et al. | 606/48 |
| 8,372,067 B2 | 2/2013 | Woloszko et al. | 606/34 |
| 2002/0029036 A1 | 3/2002 | Goble et al. | 606/38 |
| 2002/0042612 A1 | 4/2002 | Hood et al. | 606/50 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2003/0232048 A1 | 12/2003 | Yang et al. | 424/141.1 |
| 2004/0030330 A1 | 2/2004 | Brassell et al. | 606/41 |
| 2004/0116922 A1 | 6/2004 | Hovda et al. | 606/41 |
| 2004/0127893 A1 | 7/2004 | Hovda | 606/41 |
| 2004/0186418 A1 | 9/2004 | Karashima | 604/20 |
| 2004/0230190 A1 | 11/2004 | Dahla et al. | 604/41 |
| 2005/0004634 A1 | 1/2005 | Hovda et al. | 606/41 |
| 2005/0033278 A1 | 2/2005 | McClurken et al. | 606/34 |
| 2005/0245923 A1 | 11/2005 | Christopherson et al. | 606/41 |
| 2005/0261754 A1 | 11/2005 | Woloszko et al. | 606/32 |
| 2005/0273091 A1 | 12/2005 | Booth et al. | 607/99 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0161148 A1 | 7/2006 | Behnke | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |

(56) References Cited

U.S. PATENT DOCUMENTS

| | | | |
|---|---|---|---|
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0004621 A1 | 1/2008 | Dahla et al. | 606/48 |
| 2008/0077128 A1 | 3/2008 | Woloszko et al. | 606/41 |
| 2008/0138761 A1 | 6/2008 | Pond | 433/29 |
| 2008/0140069 A1 | 6/2008 | Filloux et al. | 606/41 |
| 2008/0154255 A1 | 6/2008 | Panos et al. | 606/33 |
| 2008/0167645 A1 | 7/2008 | Woloszko | 606/40 |
| 2008/0234671 A1 | 9/2008 | Marion | 606/41 |
| 2008/0243116 A1 | 10/2008 | Anderson | 606/41 |
| 2008/0300590 A1 | 12/2008 | Horne et al. | 606/35 |
| 2009/0209956 A1 | 8/2009 | Marion | 606/34 |
| 2009/0222001 A1 | 9/2009 | Greeley | 606/33 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2011/0245826 A1 | 10/2011 | Woloszko et al. | 606/41 |
| 2012/0083782 A1 | 4/2012 | Stalder et al. | 606/41 |
| 2012/0095454 A1 | 4/2012 | Cox et al. | 606/33 |
| 2012/0109123 A1 | 5/2012 | Woloszko et al. | 606/45 |
| 2012/0196251 A1 | 8/2012 | Taft et al. | 433/216 |
| 2012/0197344 A1 | 8/2012 | Taft et al. | 607/51 |
| 2012/0215221 A1 | 8/2012 | Woloszko | 606/50 |
| 2012/0296328 A1 | 11/2012 | Marion | 606/34 |
| 2013/0116680 A1 | 5/2013 | Woloszko | 606/33 |

FOREIGN PATENT DOCUMENTS

| | | | |
|---|---|---|---|
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 98/56324 | 12/1998 | |
| WO | 99/20213 | 4/1999 | |
| WO | 99/51155 | 10/1999 | A61B 17/36 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | |
| WO | 00/62685 | 10/2000 | A61B 17/20 |
| WO | 01/24720 | 4/2001 | A61B 18/18 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/102255 | 12/2002 | A61B 17/20 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2007/006000 | 1/2007 | A61B 18/14 |
| WO | 2007/056729 | 5/2007 | A61B 18/14 |
| WO | 2010/052717 | 5/2010 | A61B 18/14 |
| WO | 2012/050636 | 4/2012 | A61B 18/14 |
| WO | 2012/050637 | 4/2012 | A61B 18/14 |

OTHER PUBLICATIONS

BiLAP Generator Settings, Jun. 1991.

BiLAP IFU 910026-001 Rev A for BiLAP Model 3525, J-Hook, 4 pgs, May 20, 1991.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

Codman & Shurtleff, Inc. "The Malis Bipolar Coagulating and Bipolar Cutting System CMC-II" brochure, early, 2 pgs, 1991.

Codman & Shurtleff, Inc. "The Malis Bipolar Electrosurgical System CMC-III Instruction Manual", 15 pgs, Jul. 1991.

Cook et al., "Therapeutic Medical Devices: Application and Design", Prentice Hall, Inc., 3pgs, 1982.

Dennis et al. "Evolution of Electrofulguration in Control of Bleeding of Experimental Gastric Ulcers," Digestive Diseases and Sciences, vol. 24, No. 11, 845-848, Nov. 1979.

Dobbie, A.K., "The Electrical Aspects of Surgical Diathermy, Bio Medical Engineering" *Bio-Medical Engineering* vol. 4, pp. 206-216, May 1969.

Elsasser, V.E. et al., "An Instrument for Transurethral Resection without Leakage of Current" *Acta Medicotechnica* vol. 24, No. 4, pp. 129-134, 1976.

Geddes, "Medical Device Accidents: With Illustrative Cases" CRC Press, 3 pgs, 1998.

Honig, W., "The Mechanism of Cutting in Electrosurgery" *IEEE* pp. 58-65, 1975.

Kramolowsky et al. "The Urological App of Electorsurgery" *J. of Urology* vol. 146, pp. 669-674, 1991.

Kramolowsky et al. "Use of 5F Bipolar Electrosurgical Probe in Endoscopic Urological Procedures" *J. of Urology* vol. 143, pp. 275-277, 1990.

Lee, B et al. "Thermal Compression and Molding of Artherosclerotic Vascular Tissue with Use" JACC vol. 13(5), pp. 1167-1171, 1989.

Letter from Department of Health to Jerry Malis dated Jan. 24, 1991, 3 pgs.

Letter from Department of Health to Jerry Malis dated Jul. 25, 1985, 1 pg.

Letter from Jerry Malis to FDA dated Jul. 25, 1985, 2 pgs.

Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg.

(56) References Cited

OTHER PUBLICATIONS

Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and Streptococcus Mutans", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
O'Neill et al., "Percutaneous Plasma Discectomy Stimulates Repair in Injured Porcine Intervertebral Discs", Dept. of Orthopaedic Surgery, Dept. of Radiology University of California at San Francisco, CA, 3 pgs No date.
Rand et al., "Effect of Elecctrocautery on Fresh Human Articular Cartilage", J. Arthro. Surg., vol. 1, pp. 242-246, 1985.
European Examination Report for EP 02773432 4 pgs, Sep. 22, 2009.
European Examination Report for EP 05024974 4 pgs, Dec. 5, 2008.
European Examination Report for EP 04708664 7pgs, Sep. 7, 2009.
European Examination Report for EP 02749601.7 4pgs, Dec. 2, 2009.
European Examination Report 2 for EP 04708664 5pgs, May 3, 2010.
European Search Report for EP 02773432 3pgs, Dec. 19, 2008.
European Search Report for EP 04708664.0 5pgs, Apr. 6, 2009.
European Search Report for EP 98953859, 2 pgs, Jul. 2, 2001.
Suppl European Search Report for EP 98953859, 3 pgs, Oct. 18, 2001.
Extended European Search Report for EP09152846, 8pgs, Jan. 5, 2010.

(56) References Cited

OTHER PUBLICATIONS

European Search Report for EP 99945039.8, 3 pgs, Oct. 1, 2001.
European Search Report for EP 09152850, 2 pgs, Dec. 29, 2009.
PCT International Preliminary Examination Report for PCT/US02/19261, 3pgs, Mar. 25, 2003.
PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Jul. 7, 2000.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
Slager et al., "Electrical nerve and Muscle Stimulation by Radio Frequency Surgery: Role of Direct Current Loops Around the Active Electrode", IEEE Transactions on Biomedical engineering, vol. 40, No. 2, pp. 182-187, Feb. 1993.
European Examination Report (3rd) for EP 04708664 6pgs, Nov. 6, 2012.
UK Search Report for GB1110342.1 3pgs, Oct. 18, 2011.
UK Suppl Search Report for GB1110342.1 2pgs, Aug. 16, 2012.
PCT Notification of the International Search Report and Written Opinion for PCT/US2011/033784 11 pgs, Jul. 18, 2011.
PCT Notification of the International Search Report and Written Opinion for PCT/US2011/033761 11 pgs, Jul. 22, 2011.

\* cited by examiner

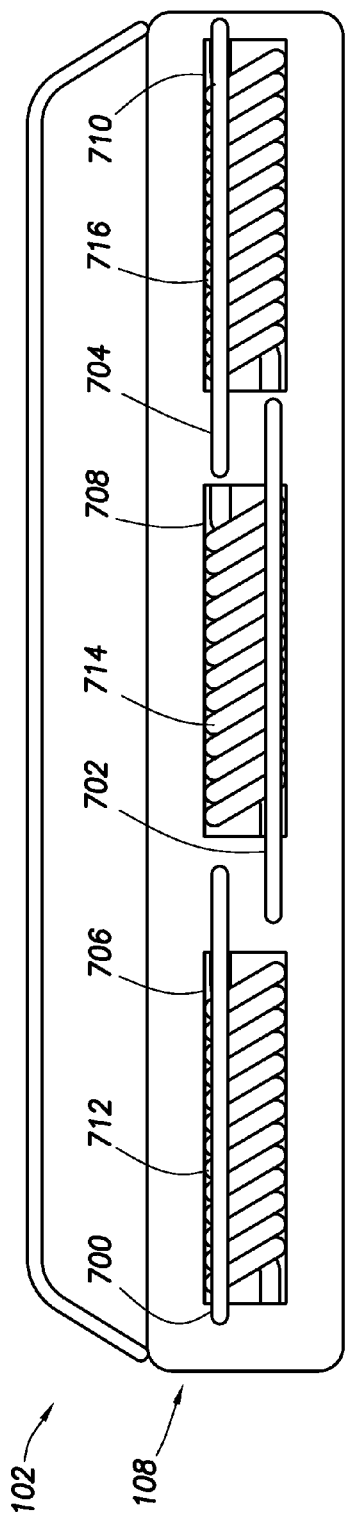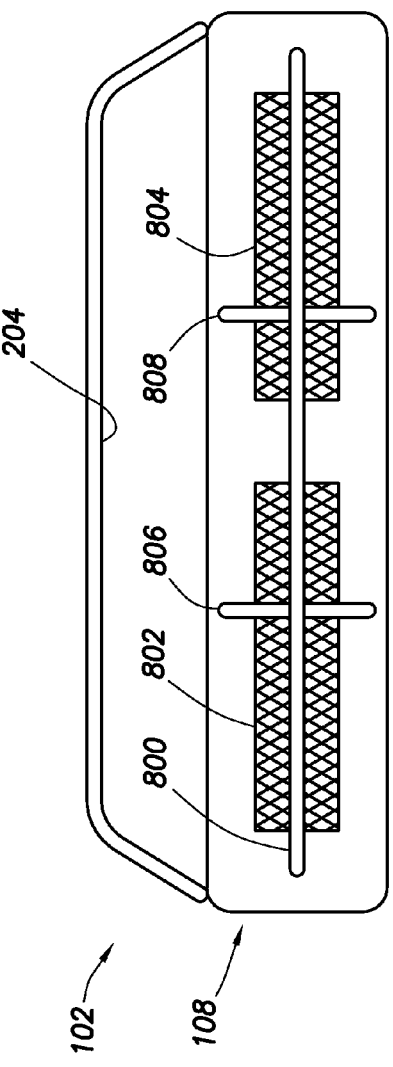

ELECTROSURGICAL WAND AND RELATED METHOD AND SYSTEM

CROSS-REFERENCE TO RELATED APPLICATIONS

None.

BACKGROUND

In the treatment of chronic wounds (e.g., diabetic foot ulcers) electrosurgical procedures may be used to promote healing. In particular, electrosurgical procedures may be used for debriding the wound, inducing blood flow to the wound, coagulating blood flow from the wound, removing necrotic tissue, and/or removing bacterial films which may form (the bacterial films sometimes referred to as "biofilm"). In many cases wounds are considered "dry" in the sense that there is insufficient conductive fluid present to support plasma creation for electrosurgical procedures. In such cases a conductive fluid (e.g., saline) is provided to help support plasma creation.

However, in providing a conductive fluid to a wound to help support plasma creation, the location of the wound and/or the orientation of the patient may adversely impact how the conductive fluid is distributed. For example, gravity may cause the conductive fluid to flow in such a way as to not fully "wet" one or more of the electrodes involved in the plasma creation, thus limiting or preventing plasma creation.

Any advance that better controls distribution of conductive fluid in and around the electrodes of an electrosurgical system would provide a competitive advantage.

BRIEF DESCRIPTION OF THE DRAWINGS

For a detailed description of exemplary embodiments, reference will now be made to the accompanying drawings in which:

FIG. 7 shows a front elevation view of a wand in accordance with at least some embodiments;

FIG. 8 shows a front elevation view of a wand in accordance with at least some embodiments;

NOTATION AND NOMENCLATURE

Figure 1:
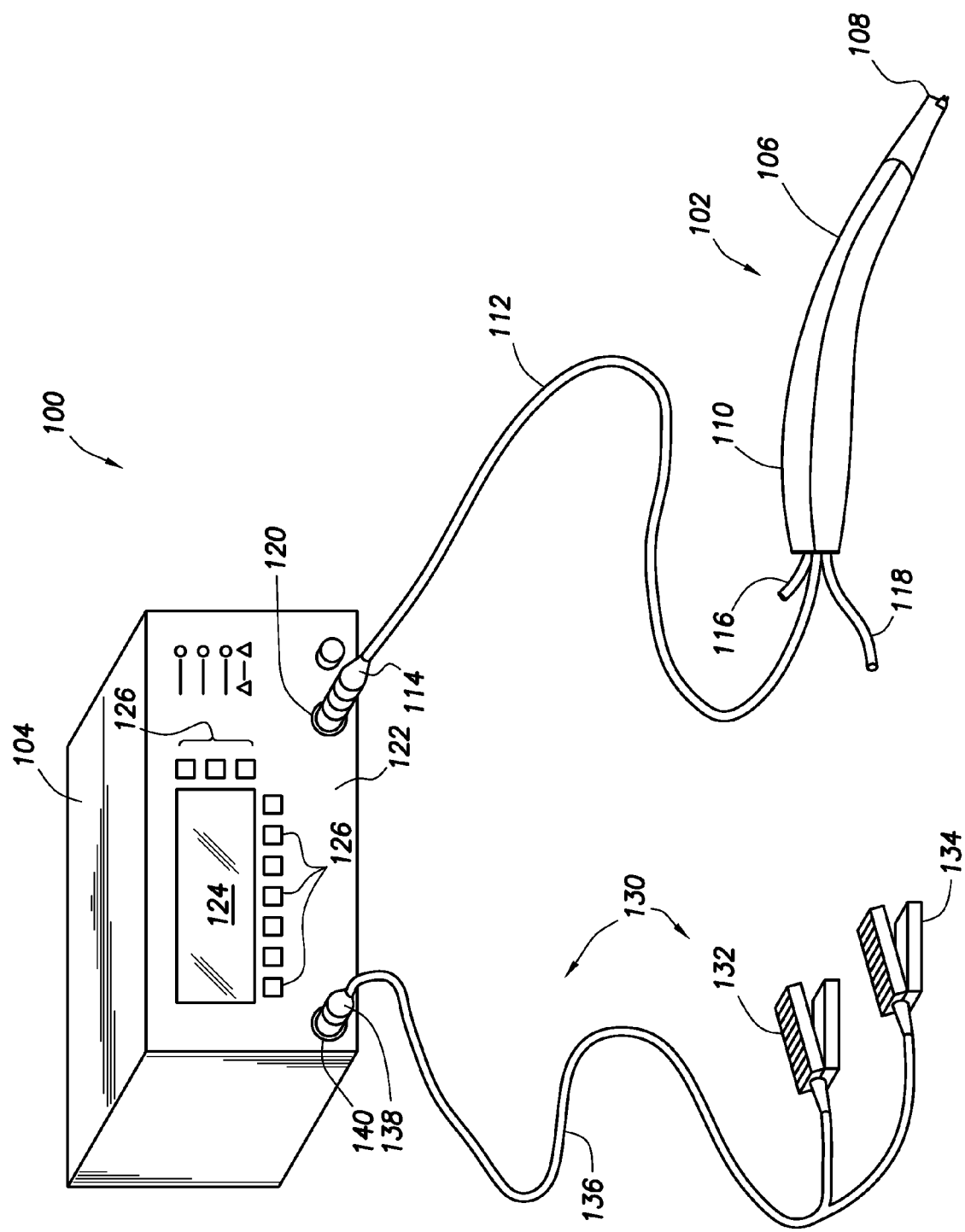
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow return path with respect to an active electrode, and/or an electrode of an electrical surgical wand which does not itself produce an electrically-induced tissue-altering effect on tissue targeted for treatment.

A fluid conduit said to be "within" an elongate housing shall include not only a separate fluid conduit that physically resides within an internal volume of the elongate housing, but also situations where the internal volume of the elongate housing is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate housing 106 that defines distal end 108 where at least some electrodes are disposed. The elongate housing 106 further defines a handle or proximal end 110. The wand 102 further comprises a flexible multi-conductor cable 112 housing a plurality of electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal lumens or fluid conduits coupled to externally accessible tubular members. As illustrated, the wand 102 has a first flexible tubular member 116 and a second flexible tubular member 118. In some embodiments, the flexible tubular member 116 is used to provide saline to the distal end 108 of the wand. Likewise in some embodiments, flexible tubular member 118 is used to provide suction for aspiration at the distal end 108 of the wand. In some embodiments, the flexible tubular member 116 is a hose having a 0.152 inch outside diameter, and a 0.108 inch inside diameter, but other sizes may be equivalently used. Further, in some embodiments the flexible tubular member 118 is a hose having a 0.25 inch outside diameter, and a 0.17 inch internal diameter, but other sizes may be equivalently used.

Still referring to FIG. 1, the controller 104 controllably provides energy to the wand 102 for the electrosurgical procedures (discussed more below). A display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. The foot pedal assembly 130 may be used to control various aspects of the controller 104, such as the operational mode. For example, a pedal device, such as pedal device 132, may be used for on-off control of the application of radio frequency (RF) energy to the wand 102. A second pedal device, such as pedal device 134, may be used to control and/or set the operational mode of the electrosurgical system. For example, actuation of pedal device 134 may switch between energy levels. In yet still further embodiments, the wand 102 may further comprises switches accessible on an outside portion, where the switches may control the operational modes of the controller 104.

The electrosurgical system 100 of the various embodiments may have a variety of operational modes. One such mode employs Coblation® technology. In particular, the assignee of the present disclosure is the owner of Coblation® technology. Coblation® technology involves the application of an RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region near the one or more active electrodes and the target tissue. Electrically conductive fluid may be inherently present in the body, such as blood, puss, or in some cases extracellular or intracellular fluid. In other embodiments, the electrically conductive fluid may be a liquid or gas, such as isotonic saline. In a particular embodiment of wound treatment, the electrically conductive fluid is delivered in the vicinity of the active electrode and/or to the target site by the wand 102, such as by way of the internal fluid conduit and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 may also in particular situations be useful for sealing blood vessels, when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue.

A more complete description of the various phenomena can be found in commonly assigned U.S. Pat. Nos. 6,355,032; 6,149,120 and 6,296,136, the complete disclosures of which are incorporated herein by reference.

Figure 2A:
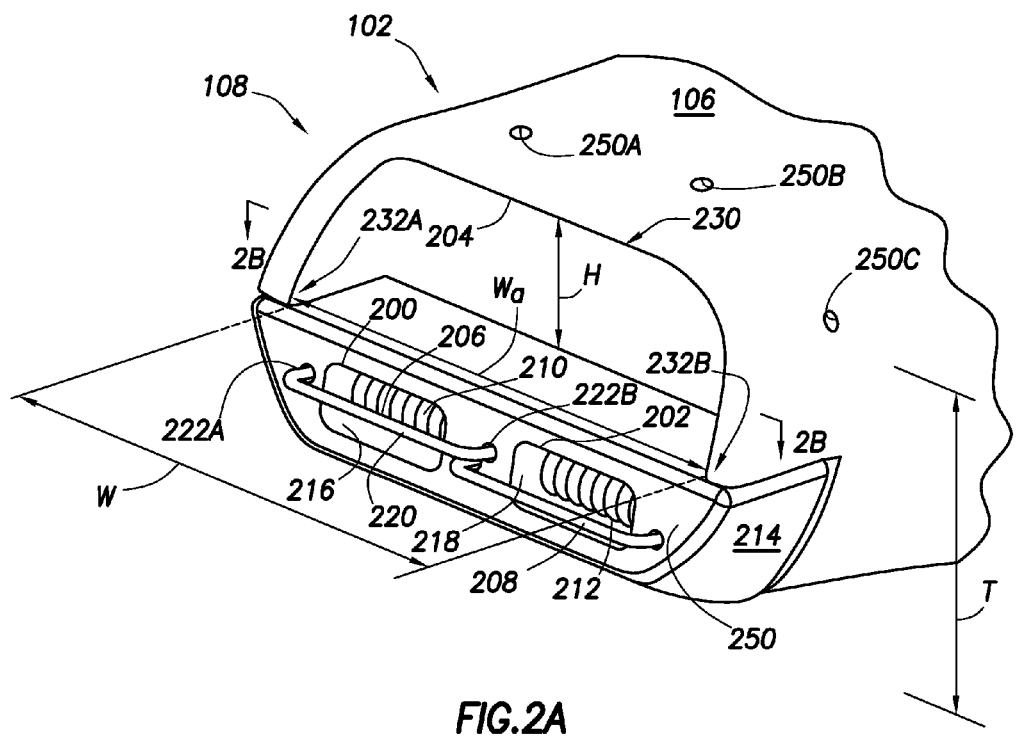
FIG. 2A shows a perspective view a portion of a wand in accordance with at least some embodiments.

FIG. 2A illustrates a perspective view of the distal end 108 of wand 102 in accordance with at least some embodiments. In particular, the illustrative system of FIG. 2A has two discharge apertures 200 and 202, an aspiration aperture 204, two active electrodes 206 and 208, two return electrodes 210 and 212, along with a support member 214. Moreover, the illustrative distal end 108 defines a width (labeled W in the figure) and a thickness (labeled T in the figure). Each of the components will be discussed in turn.

The support member 214 is coupled to the elongate housing 106. In a particular embodiment, the elongate housing 106 and handle 110 (FIG. 1) are made of a non-conductive plastic material, such as polycarbonate. In yet other embodiments, the handle 110 and/or elongate housing 106 may be constructed in whole or in part of metallic material, but for reasons discussed more below the metallic material is non-grounded and/or does not provide a return path for electrons to the controller 104. Further, support member 214 is a non-conductive material resistant to degradation when exposed to plasma. In some cases support member 214 is made of a ceramic material (e.g., alumina ceramic), but other non-conductive materials may be equivalently used (e.g., glass). An illustrative two discharge apertures 200 and 202 are defined within the support member 214. The discharge apertures are rectangular with rounded corners, and where the long dimensions of the apertures 200 and 202 are aligned with the width W. Rectangular shaped discharged apertures are merely illustrative, and any suitable shape may be equivalently used (e.g., circular, oval, square). Within the support member 214 each aperture 200 and 202 defines a fluid conduit 216 and 218, respectively. Each fluid conduit is fluidly coupled within the elongate housing 106 to flexible tubular member 116 (FIG. 1), through which conductive fluid is pumped or gravity fed during use. Thus, during use, conductive fluid flows into the flexible tubular member 116 (FIG. 1), through one or more fluid conduits (not specifically shown) within the elongate housing 106, through the fluid conduits 216 and 218 defined through the non-conductive support member 214, and out of the discharge apertures 200 and 202.

In the various embodiments, the conductive fluid has conductivity above a minimum threshold. More particularly, the conductive fluid will have conductivity greater than 0.2 milli-Siemens per centimeter (mS/cm), in some cases greater than about 2 mS/cm, and in other cases greater than about 10 mS/cm. An example of the conductive fluid that may be used is isotonic saline, having conductivity of about 17 mS/cm. During wound debridement, saline may flow at the rate of between and including 30 and 70 milli-Liters per min (mL/min), but may vary depending on factors such as: the pressure at the aspiration aperture 204; the geometry, material property and configuration of the return electrodes 210 and 212; the geometry, material properties and configuration of the active electrodes 206 and 208; and the geometry, material properties and configuration of the support member 214.

Still referring to FIG. 2A, the illustrative the distal end 108 further comprises two active electrodes 206 and 208. Each active electrode is a metallic structure, around which plasma is created during use in some operational modes. In some case, the wire is stainless steel, but other types of metallic wire (e.g., tungsten, molybdenum) may be equivalently used. As illustrated, each active electrode 206 and 208 is a loop of wire having a particular diameter. Smaller diameter wire for the active electrodes advantageously results in less thermal heating of the tissue, but there is a tradeoff with wire strength, as smaller wire diameters tend to break and/or bend more easily. In some embodiments, the wire diameter for each active electrode is between and including 0.008 and 0.015 inches, and in a particular case 0.010 inches. Using active electrode 206 as exemplary of both active electrodes, the illustrative active electrode 206 comprises a straight portion 220, as well as two standoff portions 222 (labeled 222A and 222B). In a particular embodiment (and as illustrated) the straight portion 220 resides over the respective discharge aperture 200. "Over" in this instance does not imply an orientation of the distal end 108 of the wand 102; rather, "over" is only meant to imply that if the fluid conduit 216 was projected outward past the discharge aperture 200, at least a portion of the straight portion 220 would reside within the projected area. In other cases the active electrodes need not be over the discharge apertures, so long as the active electrodes reside in the conductive fluid path between the discharge apertures 200 and 202 and the aspiration aperture 204.

In accordance with at least some embodiments, the length of the straight portion 220 is between and including 0.16 and 0.18 inches. Moreover, standoff portions 222 define an exposed length of about between and including 0.010 and 0.050 inches, and in some cases between and including 0.015 and 0.025 inches. In these embodiments the length defined by the standoff portions 222 is measured from the surface 250 defined by the support member 214 to the central axis of the straight portion 220. It will be understood, however, that the standoff portions 222 may extend into the support member 214, and thus will be longer than the exposed length. However, other straight portion 220 and standoff portion 222 lengths may be equivalently used. For the example wire diameters and lengths of this paragraph, the exposed surface area of each active electrode (i.e., that portion residing outside the non-conductive support member 214) may be between and including 0.00447 and 0.04141 square inches.

Still referring to active electrode 206 as illustrative of both active electrodes, the active electrode 206 is electrically coupled to the controller 104 (FIG. 1). In some cases, the active electrode 206 is coupled to the controller by way of one of the standoff portions 222 and an insulated conductor (not specifically shown) that runs through the elongate housing 106. Thus, by way of the cable 112 (FIG. 1) and electrical pins (shown in FIG. 9 below) in the connector 114 (FIG. 1), the active electrode 206 couples to the controller 104 (FIG. 1). In some cases the active electrodes all couple to the controller 104 by way of the same electrical pin, and in other cases each active electrode may couple to the controller by way of its own electrical pin.

The straight portions of the active electrodes in FIG. 2A are parallel. However, the arrangement of FIG. 2A is merely illustrative. The active electrodes may take any suitable shape, and any suitable orientation between them. For example, the straight portions of the active electrodes may be coaxial. Further still, straight portions of the active electrodes may form an obtuse angle. Yet further still, the active electrodes may take any suitable form, such as a sinusoid between the standoffs 222, or saw tooth pattern between the standoffs 222. In many cases, regardless of the form of the active electrodes, each active electrode 206 and 208 has approximately the same standoff distance from the plane defined by the outer surface 250 of the support member 214.

Still referring to FIG. 2A, the distal end 108 further comprises return electrodes 210 and 212 associated with each active electrode 206 and 208, respectively. Each return electrode is made of conductive material, which conductive material forms a return path for electrical current associated with energy applied to the active electrodes. In the illustrative embodiments of FIG. 2A, each return electrode 210 and 212 comprises metallic wire. In some case, the wire is stainless steel, but other types of metallic wire (e.g., titanium, molybdenum) may be equivalently used. Further, each illustrative return electrode 210 and 212 is associated with a discharge aperture 200 and 202, respectively. Using return electrode 212 as exemplary of both return electrodes, the illustrative return electrode 212 comprises the conductive material disposed within the fluid conduit 218 such that at least some of the conductive fluid flowing through the fluid conduit 218 contacts the return electrode 212 before discharging through the discharge aperture 202. In a particular embodiment, and as illustrated, the return electrode 212 resides at a sufficient distance within the fluid conduit (i.e., a recess distance) that no portion of the return electrode 212 extends through the plane defined by the discharge aperture 212. Having the return electrodes disposed within the fluid conduit 202 reduces the chances that the return electrode contacts the tissue of the treatment area, and thus reduces the chance of thermal heating. In accordance with at least some embodiments, the return electrode 212 is recessed within the fluid conduit between and including 0.020 and 0.030 inches measured from the aperture 202; however, the recess distance and the exposed length of the standoff portions 222 are related in that the distance between an active electrode and a corresponding return electrode should be 0.030 inches or greater (measured from the active to the closest exposed portion of the return electrode). Shorter distances may be operational, but there is an increased tendency for arcing directly between the active and return electrodes to occur. Thus, in embodiments where a portion of the active electrode is disposed over a discharge aperture, as the exposed length of the standoff portions is shorter, the recess distance may be increased.

As illustrated, the return electrode 212 comprises a coil of wire having an uncoiled length of between and including 0.5 to 3.0 inches. The wire diameter in these embodiments may be between and including 0.010 and 0.020 inches. For the particular case of each return electrode being a coil of wire having an uncoiled length of 1.08 inches and a diameter of 0.012 inches, the exposed surface area of each return electrode will be approximately 0.0404 square inches. In accordance with at least some embodiments, the wire diameter and length of the return electrodes are selected such that the exposed surface of the return electrodes is greater than the exposed surface area of the active electrodes. Return electrode 212 in the form of a coil of wire defines a central axis, and in the illustrative embodiments of FIG. 2 the central axis of the coil of wire is parallel to the straight portion of the loop of wire 208; however, other arrangements may be equivalently used.

Still referring to return electrode 212 as illustrative of both return electrodes, the return electrode 212 is electrically coupled to the controller 104 (FIG. 1). In some cases, the return electrode 212 is coupled to the controller by way of an insulated conductor (not specifically shown) that runs through the elongate housing 106. Thus, by way of the cable 112 (FIG. 1) and electrical pins (shown in FIG. 9 below) in the connector 114 (FIG. 1), the return electrode couples to the controller 104 (FIG. 1). In some cases the return electrodes all couple to the controller 104 by way of the same electrical pin, and in other cases each return electrode may couple to the controller by way of its own electrical pin.

Having the return electrodes 210 and 212 within the fluid conduits 216 and 218, respectively, aids in operation of the wand 102 for wound care in several ways. First, having the return electrodes 210 and 212 within the fluid conduits 216 and 218, respectively, increases the likelihood that the conductive fluid used to wet the electrodes makes good contact with both the active and return electrodes in spite of the orientation of the wand 102. Stated otherwise, regardless of the orientation of the wand 102 with respect to gravity, the conductive fluid provided to the wound treatment site has a better chance of contacting both return electrodes. By comparison, wands that implement the return electrode by way of conductive material on a shaft may have difficulty ensuring good wetting of both the active and return electrodes by way of the conductive fluid in some physical orientations. Second, placement of the return electrodes 210 and 212 in the fluid conduits 216 and 218, respectively, helps diffuse the conductive fluid proximate the distal end 108 of the wand 102, which further aids in ensuring good wetting, particularly wetting of the associated active electrodes.

FIG. 2A also illustrates that a wand 102 in accordance with at least some embodiments further comprises an aspiration aperture 204. The aspiration aperture 204 is fluidly coupled to the flexible tubular member 118 (FIG. 1) by way of fluid conduit (not specifically shown) within the wand 102. Thus, and as the name implies, the aspiration aperture 204 is used to remove byproducts of wound treatment using the wand 102, such as removal of excess conductive fluid, molecularly disassociated tissue, and tissue separated from the wound but otherwise still intact. As illustrated, the aspiration aperture 204 has a width "$W_a$" approximately the same as the support member 214, and thus slightly wider than the active electrodes. Moreover, in some embodiments the height "H" of the aspiration aperture is a function of the standoff distance of the active electrodes. In some cases the height H may be greater than or equal to three times (i.e., 3 to 1) the exposed length of the standoff portions, in other cases greater than or equal to six times (i.e., 6 to 1) the exposed length of the standoff portions, and in yet further cases greater than or equal to ten times (i.e., 10 to 1) the exposed length of the standoff portions. For example, with an exposed length of the standoff portions being in the range 0.015 to 0.025 inches, and a 6-to-1 relationship, the aspiration aperture height may be on the order 0.09 to 0.155 inches, respectively.

In operation of the various embodiments, aggressive aspiration is contemplated to help remove larger pieces of tissue not molecularly disassociated (discussed more below). In some cases, the aspiration may be created by an applied pressure between and including 100 millimeters of mercury (mmHg) and 400 mmHg below atmospheric. However, in some cases aggravation of an existing wound may occur if the aspiration aperture 204 is allowed to seal against the wound. In order to reduce the possibility of the aspiration aperture 204 sealing against the wound and/or patient, and as illustrated, in some embodiments at least a portion of the aspiration aperture is closer to the handle 110 (FIG. 1) than any portion of the discharge apertures. In particular, portion 230 is closer to the handle than portions 232A and 232B. Thus, when the distal end 108 is held in an orientation where the active electrodes 206 and 208 can interact with the wound, the likelihood of the aspiration aperture 204 sealing against the wound and/or patient are drastically reduced. In yet still further embodiments, optional apertures 250 (three illustrative apertures labeled 250A through 250C) may be implemented to ensure that if, by chance, the aperture 204 seals against the wound, the wound will not be subjected to the full force of the aspiration suction as air may flow into the apertures 250. Other mechanisms to reduce the likelihood of sealing of the aperture as discussed below.

Figure 2B:
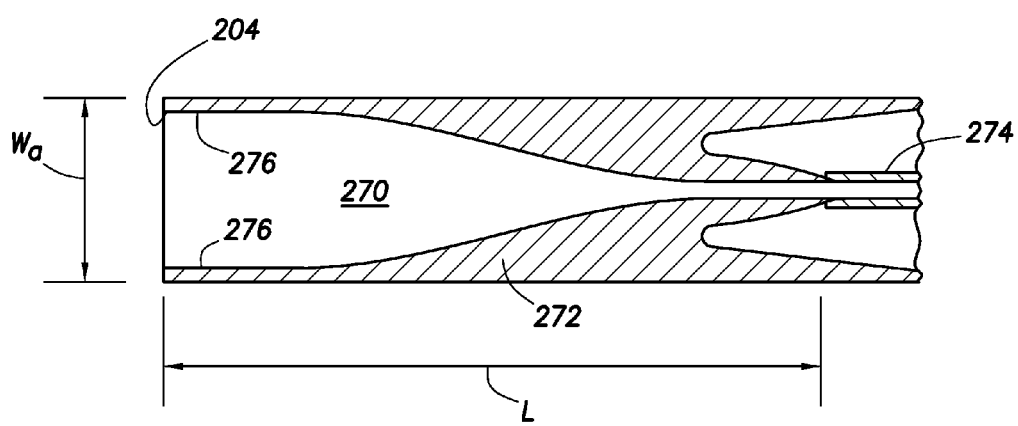
FIG. 2B shows a partial cross-sectional view taken substantially along line 2B-2B of FIG. 2A.

FIG. 2B shows an overhead cross-sectional view taken substantially along lines 2B-2B of FIG. 2A. In particular, FIG. 2B shows the aspiration aperture 204 as well as a fluid conduit 270 defined by walls 272. In operation, suction is provided to the flexible tubular member 116 (FIG. 1), and flexible tubular member 118 either extends into the internal volume of the wand 102 to become, or fluidly couples to, internal lumen 274. Thus, conductive fluid, molecularly disassociated tissue, as well as tissue pieces (discussed more below), are drawn through the aspiration aperture 204, into the fluid conduit 270, and eventually into the lumen 274. The inventors of the present specification have found that particular length of the fluid conduit 270 between aspiration aperture 204 and the entrance to the internal lumen 274 work better than others. For example, if the length is too short, the fluid conduit 270 is subject to clogging. Likewise, if the length is too long, zones of little or no airflow develop, again leading to clogging. In accordance with at least some embodiments the length of the fluid conduit 270 between the aperture 204 and the entrance to the internal lumen 274 is a function of the width $W_a$ of the aspiration aperture at the widest point. More particularly, in accordance with at least some embodiments the internal walls 276 that define the fluid conduit 270 should be smoothly varying, and the length "L" over which the width changes should be at least two times the change in width, and in most cases not longer than eight times the change in width. Consider, as an example, a wand where the $W_a$ is 0.39 inches (about 10 millimeters (mm)), and the internal diameter of the lumen 274 is 0.118 inches (3 mm). In such a situation the change in internal width of the fluid conduit 270 between the aspiration aperture 204 and the entrance to the lumen 274 will be about 0.272 inches (about 7 mm), and in at least some embodiments the length L over which the change in width is implemented should be at least 0.544 inches (at least 14 mm). In a particular embodiment the change in internal width to the length L is related as:

$$L=(W_a-\text{ID})*2.3 \qquad (1)$$

where ID is the internal diameter of the lumen 274. Thus, for example, a fluid conduit 270 associated with an aspiration aperture in operational relationship to a wand 102 with a single active electrode will have a shorter length than in the transition to the internal lumen than a fluid conduit 270 associated with an aspiration aperture in operational relationship to a wand 102 with three or more active electrodes.

The inventors present the characteristic of the length L of FIG. 2B in terms of the width $W_a$ of the aspiration aperture for sake of simplicity. Further, equivalent, relationships may be determined, for example, based on changes in cross-sectional area of the fluid conduit 270 taking into account the height H (FIG. 2A) in relation to the standoff distances implemented by the standoff portions 222. Moreover, while FIG. 2B shows each wall 276 of the fluid conduit 270 to be smoothly varying similar to a tangent function (i.e., asymptotically approaching the $W_a$ on one end, and asymptotically approaching the internal diameter of the lumen 252 on the other), other smoothly varying internal surfaces may be equivalently used (e.g., straight line change in $W_a$ from the aperture 204 to the internal diameter of the lumen 252, asymptotically approaching the internal diameter of the lumen 252).

Figure 3:
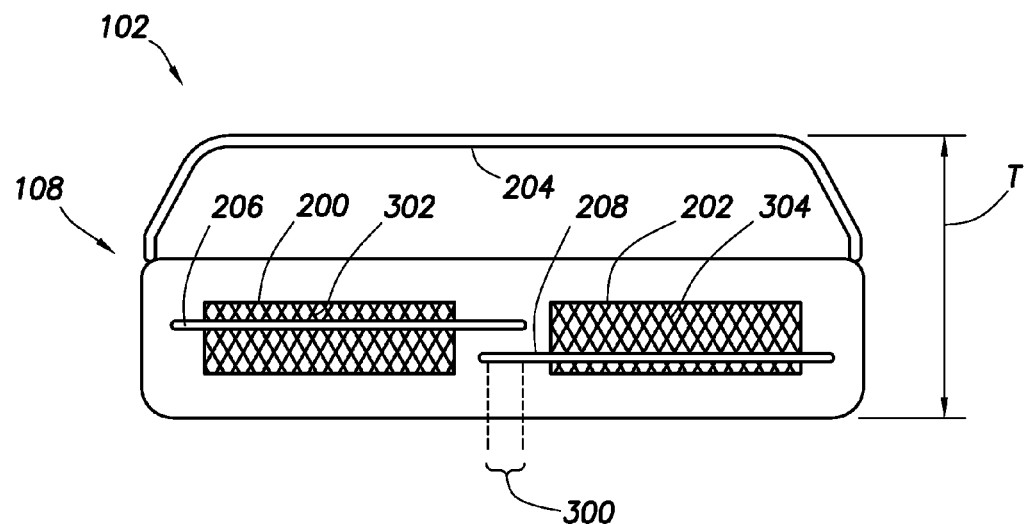
FIG. 3 shows a front elevation view of a wand in accordance with at least some embodiments.

FIG. 3 shows a front elevation view of the distal end 108 of the wand 102 in accordance with at least some embodiments. In particular, the view of FIG. 3 better shows the relationship of the active electrodes 206 and 208 to the discharge apertures 200 and 202, respectively. Active electrode 206 is shown over the discharge aperture 200. Likewise, active electrode 208 is over the discharge aperture 202. Thus, as conductive fluid is discharged through the discharge apertures 200 and 202, the chance the conductive fluid will contact the active electrodes is high, regardless of the orientation of the wand 102 in relation to gravity. Again, however, in other embodiments the active electrodes need not be disposed over the discharge apertures.

In FIG. 3, the active electrodes are offset along the thickness T. In particular, active electrode 206 is closer to the aspiration aperture 204 than active electrode 208. While in some embodiments the active electrodes have the same elevation with respect to the thickness T, in the illustrative embodiments there is an overlap 300. The overlap 300 of the active electrodes ensures that, in operation, the surface left within the wound is less likely to have any ridges or elevation changes caused by non-uniformity of the active electrodes.

FIG. 3 also illustrates alternative return electrodes. In particular, FIG. 3 illustrates return electrodes in form of a metallic wire mesh. Wire mesh 302 resides within the fluid conduit defined by discharge aperture 200, and wire mesh 304 resides within the fluid conduit defined by discharge aperture 202. In some cases, the wire mesh is placed such that no portion of the wire mesh extends beyond a plane defined by the aspiration apertures 200 and 202, to reduce the chances of the return electrodes contacting tissue of the wound. As with the return electrodes in the form of a coil of wire, the wire mesh return electrodes 302 and 304 residing within the fluid conduits ensure good wetting of the return electrodes during use regardless of the orientation of the wand 102 during use. Moreover, the wire mesh return electrodes 302 and 304 diffuse the conductive fluid flow, which again increases the likelihood of good wetting of the respective active electrodes. The wire mesh return electrodes 302 and 304 define an exposed surface area, and in at least some embodiments the surface area of the wire mesh return electrodes is greater than the exposed surface area of the active electrodes 206 and 208.

Figure 4:
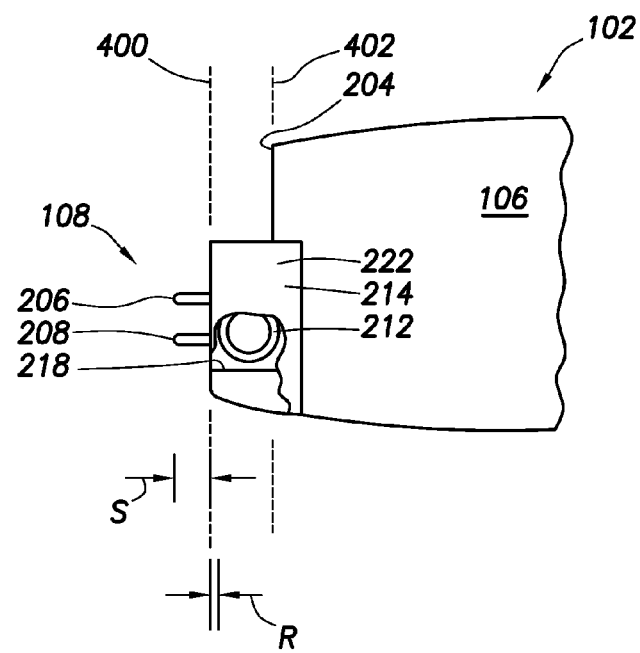
FIG. 4 shows a side elevation, with partial cut-away, view of a wand in accordance with at least some embodiments.

FIG. 4 shows a side elevation view of the distal end 108 of a wand 102, and including a partial cut-away in the area of the return electrode 212, in accordance with various embodiments. In the view of FIG. 4, the offset of the active electrodes 206 and 208 to enable the overlap 300 (not shown in FIG. 4) is visible. Here again, while FIG. 4 shows the active electrodes 206 and 208 to be parallel, other embodiments, including embodiments with overlap, may be fashioned where the outer portions of the active electrodes form an angle of greater or lesser than 180 degrees. FIG. 4 also shows the exposed length of the standoff portions 222 (labeled "S" in the figure), as well as the recess of the illustrative return electrode 212 within the fluid conduit 218 (labeled "R" in the figure).

FIG. 4 further illustrates a relationship between the face of the support member 214 and the aspiration aperture 204 in accordance with at least some embodiments. In particular, in order to reduce the likelihood of the aspiration aperture 204 sealing against the wound, in the embodiments illustrated by FIG. 4 the aspiration aperture 204 is offset toward the handle end of the wand 102. More particularly, the front face of the support member 214 defines a plane 400, and the aspiration aperture defines a plane 402. The planes 400 and 402 are parallel in the embodiments of FIG. 4, and the plane 402 associated with the aspiration aperture 214 is closer to the handle 110 (FIG. 1) than the plane 400. In some embodiments, the offset between the two illustrative planes may be between and including 0.030 and 0.060 inches.

Figure 5:
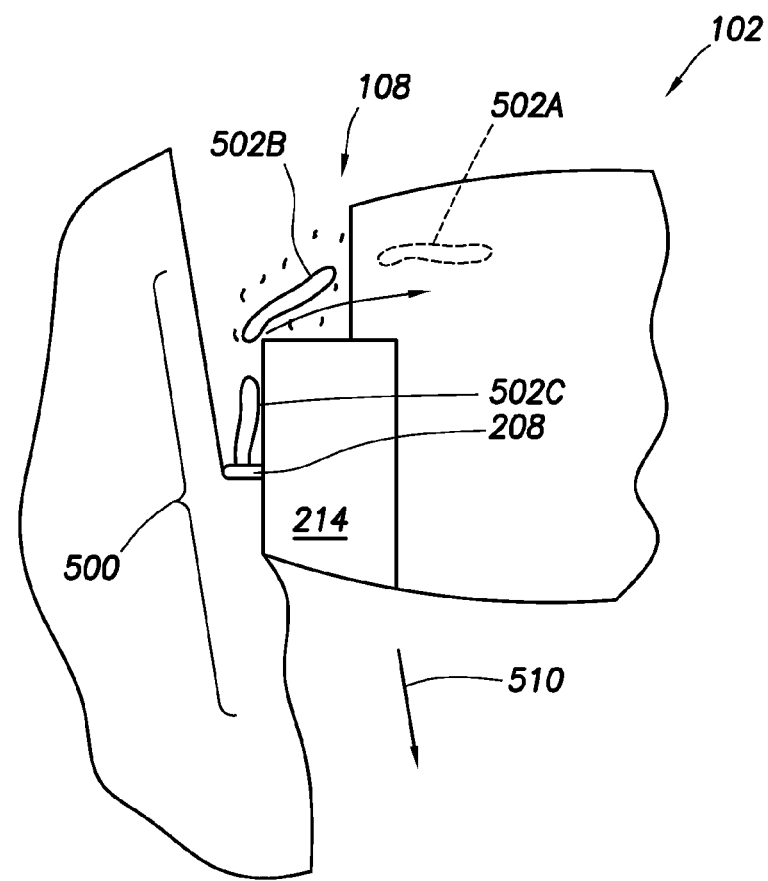
FIG. 5 a side elevation view of a wand in operational relationship to a wound in accordance with at least some embodiments.

FIG. 5 shows a side elevation view of the distal end 108 of wand 102 in use for wound care. In particular, the wand 102 is shown physically abutting wound 500, such as diabetic foot ulcer, and FIG. 5 also illustrates the wand 102 ablating portions of the wound 500. In operation, electrical energy is applied to the active electrodes, but here only active electrode 208 is visible. The energy in the example of FIG. 5 is sufficient to create plasma near the active electrodes, which thus molecularly disassociates tissue that comes in relatively close contact with the active electrodes. However, the arrangement of the active electrodes is such that the reach of the plasma is less than the exposed standoff distance of each active electrode from the plane defined by the front face of the support member 214. Thus, when operated with sufficient energy to create plasma, as the wand is translated along the wound (as illustrated by arrow 510) the active electrodes act to slice portions of the tissue, rather than attempting to completely molecularly disassociate the tissue. The result is strips of tissue 502 (multiple strips labeled 502A through 502C) are created, and which strips of tissue 502 (as well as conductive fluid and remnants of tissue molecularly disassociated) are drawn into the aspiration aperture 204 by the aspiration action. The inventors of the present specification have found that the situation illustrated by FIG. 5 is particularly efficient at debridement of wounds (e.g., removing biofilm). While not wanting to be tied to any particular theory of why the treatment works well, it is believed that the plasma created by the wand 102 is particularly efficient at destroying bacteria. Moreover, it is believed that the "slicing" action in combination with the aggressive aspiration helps ensure that the potentially bacteria contaminated strips of tissue 502 either: do not contact the remaining wound portions after removal because of motion and aspiration (thus reducing the chances of re-infecting the wound); or, if contact is present, that the contact is for such a short duration, or the contact is on side of the strips of tissue where bacterial have been killed by the plasma, that the chances of re-infection of the wound 500 are low.

Figure 6:
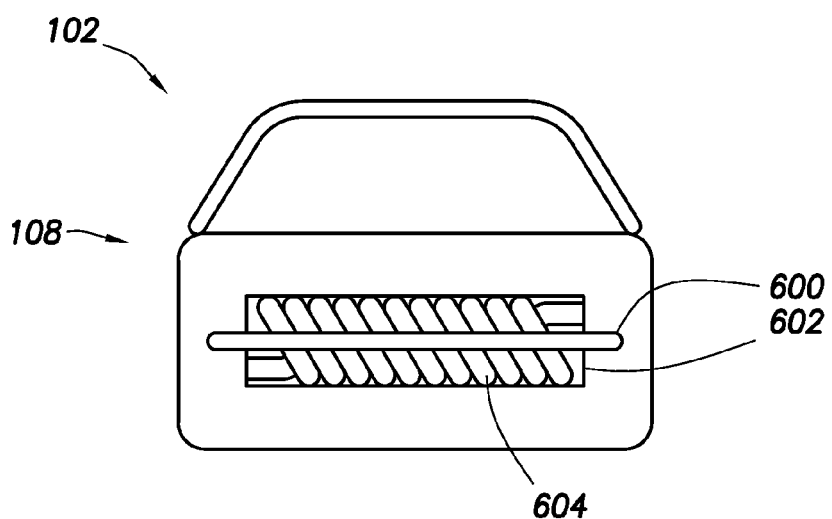
FIG. 6 shows a front elevation view of a wand in accordance with at least some embodiments.

The various embodiments discussed to this point have had two active electrodes corresponding to two discharge apertures and two return electrodes disposed within fluid conduits defined by the discharge apertures. However, other numbers of active electrodes and corresponding structure may be equivalently used. For example, FIG. 6 shows an end elevation view of the distal end 108 of wand 102 comprising a single active electrode 600 positioned over a single discharge aperture 602 and a single return electrode 604 disposed within the fluid conduit defined by the discharge aperture. Likewise, FIG. 7 shows an end elevation view of the distal end 108 of wand 102 comprising an illustrative three active electrodes 700, 702 and 704 disposed over a three discharge apertures 706, 708 and 710, respectively. Much like the other embodiments, each discharge aperture 706, 708 and 710 defines a fluid conduit, and within the fluid conduit resides three return electrodes 712, 714 and 716, respectively. One may use the wand 102 having a distal end 108 as shown in FIG. 6 as the situation dictates, for example for smaller wounds or wounds in hard to reach locations. Likewise, one may use the wand 102 having a distal end 108 as shown in FIG. 7 as the situation dictates, for example larger wounds and/or areas easier to reach.

The various embodiments discussed to this point have all shown a single active electrode spanning a single discharge aperture; however, in other configurations an active electrode may span multiple discharge apertures. FIG. 8 shows an end elevation view of the distal end 108 of wand 102 in accordance with other embodiments. In particular, FIG. 8 shows an active electrode 800 that spans two distinct discharge apertures 802 and 804. FIG. 8 also shows optional active electrodes 806 and 808, disposed perpendicularly to the active electrode 800. The optional active electrodes 806 and 808 may be used to reduce the size of the tissue pieces to be taken into the aspiration aperture 204 by the aspiration.

Figure 9:
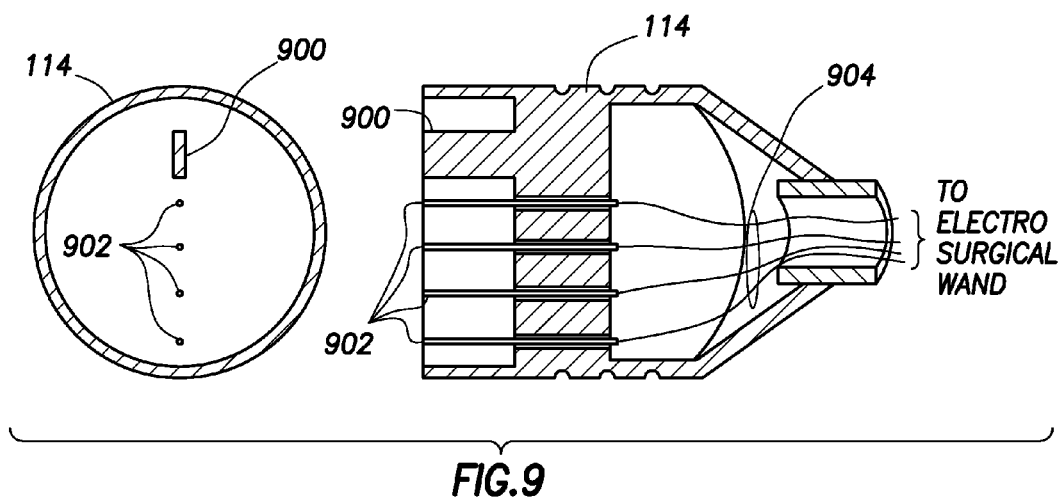
FIG. 9 shows both an elevation end-view (left) and a cross-sectional view (right) of a wand connector in accordance with at least some embodiments.

As illustrated in FIG. 1, flexible multi-conductor cable 112 (and more particularly its constituent electrical leads) couple to the wand connector 114. Wand connector 114 couples the controller 104, and more particularly the controller connector 120. FIG. 9 shows both a cross-sectional view (right) and an end elevation view (left) of wand connector 114 in accordance with at least some embodiments. In particular, wand connector 114 comprises a tab 900. Tab 900 works in conjunction with a slot on controller connector 120 (shown in FIG. 10) to ensure that the wand connector 114 and controller connector 120 only couple in one relative orientation. The illustrative wand connector 114 further comprises a plurality of electrical pins 902 protruding from wand connector 114. In many cases, the electrical pins 902 are coupled one each to an electrical lead of electrical leads 904, which leads are electrically coupled to active and return electrodes. Stated otherwise, in a particular embodiment each electrical pin 902 couples to a single electrical lead, and thus each illustrative electrical pin 902 couples to a single electrode of the wand 102. In other cases, a single electrical pin 902 couples to multiple electrodes (e.g., multiple active electrodes, or multiple return electrodes) on the electrosurgical wand 102. While FIG. 9 shows four illustrative electrical pins, in some embodiments as few as two electrical pins, and as many as 26 electrical pins, may be present in the wand connector 114.

Figure 10:
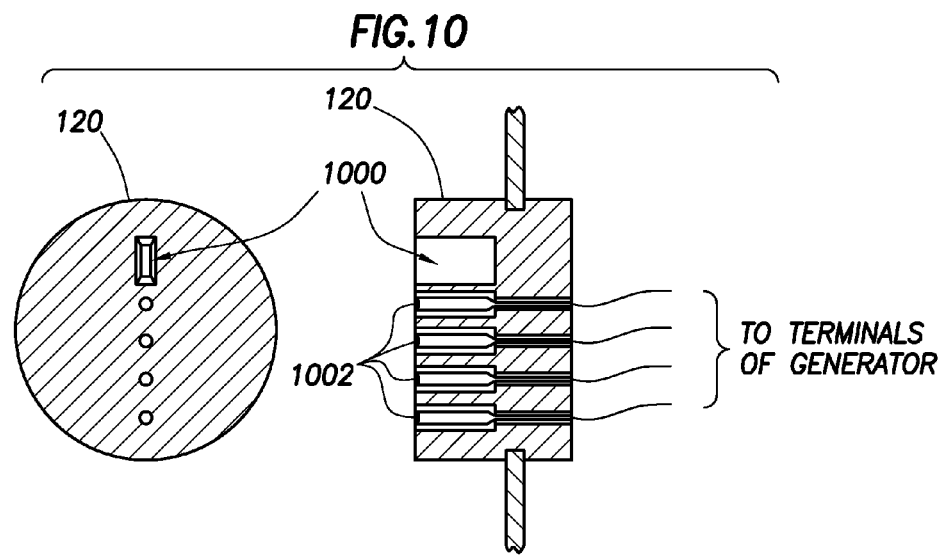
FIG. 10 shows both an elevation end-view (left) and a cross-sectional view (right) of a controller connector in accordance with at least some embodiments.

FIG. 10 shows both a cross-sectional view (right) and end elevation view (left) of controller connector 120 in accordance with at least some embodiments. In particular, controller connector 120 comprises a slot 1000. Slot 1000 works in conjunction with a tab 900 on wand connector 114 (shown in FIG. 9) to ensure that the wand connector 114 and controller connector 120 only couple in one orientation. The illustrative controller connector 120 further comprises a plurality of electrical pins 1002 residing within respective holes of controller connector 120. The electrical pins 1002 are coupled to terminals of a voltage generator within the controller 104 (discussed more thoroughly below). When wand connector 114 and controller connector 120 are coupled, each electrical pin 1002 couples to a single electrical pin 902. While FIG. 10 shows only four illustrative electrical pins, in some embodiments as few as two electrical pins and as many as 26 electrical pins may be present in the wand connector 120.

While illustrative wand connector 114 is shown to have the tab 900 and male electrical pins 902, and controller connector 120 is shown to have the slot 1000 and female electrical pins 1002, in alternative embodiments the wand connector has the female electrical pins and slot, and the controller connector 120 has the tab and male electrical pins, or other combination. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used.

Figure 11:
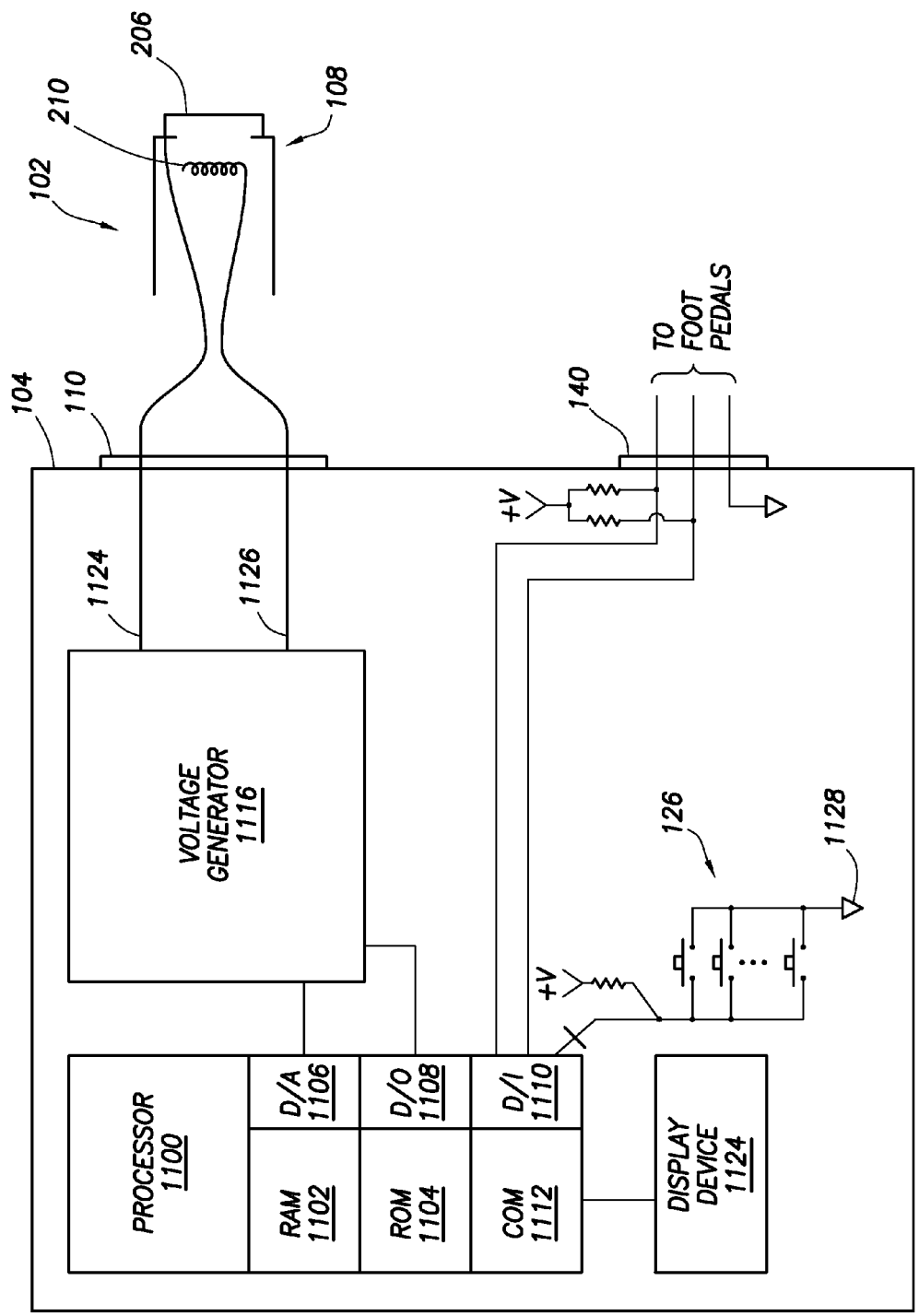
FIG. 11 shows an electrical block diagram of an electrosurgical controller in accordance with at least some embodiments.

FIG. 11 illustrates a controller 104 in accordance with at least some embodiments. In particular, the controller 104 comprises a processor 1100. The processor 1100 may be a microcontroller, and therefore the microcontroller may be integral with random access memory (RAM) 1102, read-only memory (ROM) 1104, digital-to-analog converter (D/A) 1106, digital outputs (D/O) 1108 and digital inputs (D/I) 1110. The processor 1100 may further provide one or more externally available peripheral busses, such as a serial bus (e.g., I$^2$C), parallel bus, or other bus and corresponding communication mode. The processor 1100 may further be integral with a communication logic 1112 to enable the processor 1100 to communicate with external devices, as well as internal devices, such as display device 124. Although in some embodiments the controller 104 may implement a microcontroller, in yet other embodiments the processor 1100 may be implemented as a standalone central processing unit in combination with individual RAM, ROM, communication, D/A, D/O and D/I devices, as well as communication port hardware for communication to peripheral components.

ROM 1104 stores instructions executable by the processor 1100. In particular, the ROM 1104 may comprise a software program that implements the various embodiments of controlling the voltage generator 1116 (responsive to commands from the user), as well as interfacing with the user by way of the display device 124 and/or the foot pedal assembly 130 (FIG. 1). The RAM 1102 may be the working memory for the processor 1100, where data may be temporarily stored and from which instructions may be executed. Processor 1100 couples to other devices within the controller 104 by way of the D/A converter 1106 (e.g., the voltage generator 1116), digital outputs 808 (e.g., the voltage generator 1116), digital inputs 1110 (i.e., push button switches 126, and the foot pedal assembly 130 (FIG. 1)), and other peripheral devices.

Voltage generator 1116 generates selectable alternating current (AC) voltages that are applied to the electrodes of the wand 102. In various embodiments, the voltage generator defines two terminals 1124 and 1126. The terminals 1124 and 1126 may couple to active electrodes and return electrodes. As an example, terminal 1124 couples to illustrative active electrode 206 and terminal 1126 couples to return electrode 210. In accordance with the various embodiments, the voltage generator generates an alternating current (AC) voltage across the terminals 1124 and 1126. In at least some embodiments the voltage generator 1116 is electrically "floated" from the balance of the supply power in the controller 104, and thus the voltage on terminals 1124, 1126, when measured with respect to the earth ground or common (e.g., common 1128) within the controller 104, may or may not show a voltage difference even when the voltage generator 1116 is active.

The voltage generated and applied between the active terminal 1124 and return terminal 1126 by the voltage generator 1116 is a RF signal that, in some embodiments, has a frequency of between about 5 kilo-Hertz (kHz) and 20 Mega-Hertz (MHz), in some cases being between about 30 kHz and 2.5 MHz, often between about 100 kHz and 200 kHz. The RMS (root mean square) voltage generated by the voltage generator 816 may be in the range from about 5 Volts (V) to 1000 V, preferably being in the range from about 10 V to 500 V, often between about 100 V to 350 V depending on the active electrode size and the operating frequency. The peak-to-peak voltage generated by the voltage generator 1116 for ablation for wound treatment in some embodiments is a square wave form in the range of 10 V to 2000 V and in some cases in the range of 100 V to 1800 V and in other cases in the range of about 28 V to 1200 V, often in the range of about 100 V to 320V peak-to-peak (again, depending on the electrode size and the operating frequency).

Still referring to the voltage generator 1116, the voltage generator 1116 delivers average energy levels ranging from several milliwatts to hundreds of watts per electrode, depending on the voltage applied for the target tissue being treated, and/or the maximum allowed temperature selected for the wand 102. The voltage generator 1116 is configured to enable a user to select the voltage level according to the specific requirements of a particular procedure. A description of one suitable voltage generator 1116 can be found in commonly assigned U.S. Pat. Nos. 6,142,992 and 6,235,020, the complete disclosure of both patents are incorporated herein by reference for all purposes.

In some embodiments, the various operational modes of the voltage generator 1116 may be controlled by way of digital-to-analog converter 1106. That is, for example, the processor 1100 may control the output voltage by providing a variable voltage to the voltage generator 1116, where the voltage provided is proportional to the voltage generated by the voltage generator 1116. In other embodiments, the processor 1100 may communicate with the voltage generator by way of one or more digital output signals from the digital output 1108 device, or by way of packet based communications using the communication device 1112 (connection not specifically shown so as not to unduly complicate FIG. 11).

Figure 12:
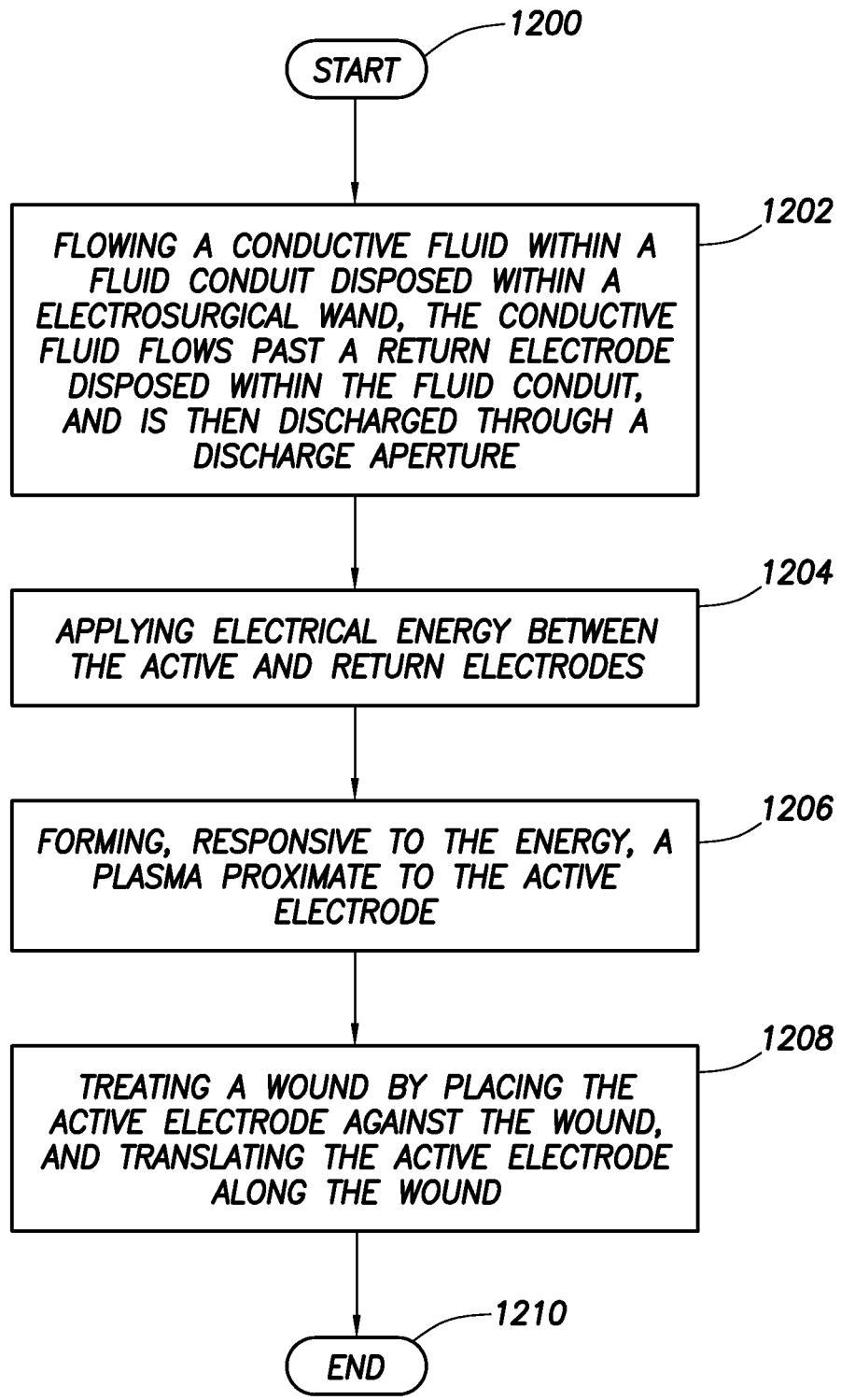
FIG. 12 shows a method in accordance with at least some embodiments.

FIG. 12 shows a method in accordance with at least some embodiments. In particular, the method starts (block 1200) and proceed to: flowing a conductive fluid within a fluid conduit disposed within a electrosurgical wand, the conductive fluid flows past a return electrode disposed within the fluid conduit, and is then discharged through a discharge aperture (block 1202); applying electrical energy between an active electrode and the return electrode (block 1204); forming, responsive to the energy, a plasma proximate to the active electrode (block 1206); and treating a wound by placing the active electrode against the wound, and translating the active electrode along the wound (block 1208).

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand comprising:
    an elongate housing that defines a handle end and a distal end;
    a connector comprising a first and second electrical pins;
    a first discharge aperture on the distal end of the elongate housing, the first discharge aperture fluidly coupled to a first fluid conduit, and the first fluid conduit within the elongate housing;
    a first active electrode of conductive material disposed on the distal end of the elongate housing, and the first active electrode electrically coupled to the first electrical pin;
    a first return electrode of conductive material completely disposed within the first fluid conduit and recessed proximally from the first discharge aperture, the first return electrode within at least a portion of a fluid path directed through and to contact the first return electrode before discharging through the first discharge aperture toward the first active electrode, and the first return electrode electrically coupled to the second electrical pin; and
    an aspiration aperture on the distal end of the elongate housing fluidly coupled to a second fluid conduit, the second fluid conduit within the elongate housing.

2. The electrosurgical wand of claim 1 wherein at least a portion of the first active electrode extends over the first discharge aperture.

3. The electrosurgical wand of claim 1 wherein the return electrode is at least one selected from the group consisting of: a coil of wire; and a wire mesh.

4. The electrosurgical wand of claim 1 wherein first active electrode further comprises a loop of wire.

5. The electrosurgical wand of claim 4 wherein the first active electrode has a standoff distance between and including 0.010 and 0.050 inches.

6. The electrosurgical wand of claim 4 wherein the first active electrode has a standoff distance of between and including 0.015 and 0.025 inches.

7. The electrosurgical wand of claim 4 wherein the loop of wire has a diameter of between and including 0.008 and 0.015 inches.

8. The electrosurgical wand of claim 4 wherein the loop of wire has a diameter of 0.010 inches.

9. The electrosurgical wand of claim 4 wherein the return electrode is a coil of wire that defines a central axis, and wherein the first active electrode defines a straight portion and the central axis is parallel to the straight portion.

10. The electrosurgical wand of claim 1 wherein at least a portion of the aspiration aperture is closer to the handle than the any portion of the discharge aperture.

11. The electrosurgical wand of claim 1 further comprising:
    a first plane defined by the discharge aperture;
    a second plane defined by the aspiration aperture; and
    wherein the first and second plane are parallel, and the second plane is closer to the handle than the first plane.

12. The electrosurgical wand of claim 1 wherein the aspiration aperture defines an aperture width, and wherein the second fluid conduit transitions in width from the aperture width to an internal width over a length not less than two times the difference between the aperture width and the internal width.

13. The electrosurgical wand of claim 1 further comprising:
    a second discharge aperture on the distal end of the elongate housing, the second discharge aperture distinct from the first discharge aperture, and the second aperture fluidly coupled to a second fluid conduit;
    a second active electrode of conductive material disposed on the distal end of the elongate housing; and
    a second return electrode of conductive material disposed within the second fluid conduit proximate to the second aperture such that at least some fluid flowing in the second fluid conduit contacts the second return electrode before discharging through the second discharge aperture toward the second active electrode.

14. The electrosurgical wand of claim 13 further comprising:
    the distal end of the elongate housing defines a width and a thickness;
    wherein first active electrode further comprises a loop of wire that defines a first outer portion;
    wherein second active electrode further comprises a loop of wire that defines a second outer portion; and
    the first and second outer portions are aligned along the width such that, when viewed along the thickness, the first and second straight portions overlap.

15. The electrosurgical wand of claim 14 further comprising:
    the first outer portion defines a first straight portion;
    the second outer portion defines a second straight portion; and
    wherein the first and second straight portions are parallel.

16. The electrosurgical wand of claim 1 further comprising:
    the first active electrode defines a first exposed surface area; and
    the first return electrode defines a second exposed surface area greater than the first exposed surface area.

17. A system comprising:
    an electrosurgical controller, the electrosurgical controller configured to produce radio frequency (RF) energy at an active terminal with respect to a return terminal;
    an electrosurgical wand coupled to the electrosurgical controller, the electrosurgical wand comprising:
        an elongate housing that defines a handle end and a distal end;
        a first discharge aperture on the distal end of the elongate housing, the first discharge aperture fluidly coupled to a first fluid conduit, and the first fluid conduit within the elongate housing;
        a first active electrode of conductive material disposed on the distal end of the elongate housing, and the first active electrode electrically coupled to the active terminal;
        a first return electrode of conductive material completely disposed within the first fluid conduit and recessed proximally from the first discharge aperture, the first return electrode within at least a portion of a fluid path directed through and to contact the first return electrode before discharging through the first discharge aperture toward the first active electrode, and the first return electrode electrically coupled to the return terminal; and an aspiration aperture on the distal end of the elongate housing fluidly coupled to a second fluid conduit, the second fluid conduit within the elongate housing.

18. The system of claim 17 wherein at least a portion of the first active electrode extends over the first discharge aperture.

19. The system of claim 17 wherein the return electrode is at least one selected from the group consisting of: a coil of wire; and a wire mesh.

20. The system of claim 17 wherein first active electrode further comprises a loop of wire.

21. The system of claim 20 wherein the first active electrode has a standoff distance of between and including 0.015 and 0.025 inches.

22. The system of claim 20 wherein the loop of wire has a diameter of 0.010 inches.

23. The system of claim 17 wherein the aspiration aperture defines an aperture width, and wherein the second fluid conduit transitions in width from the aperture width to an internal width over a length not less than two times the different between the aperture width and the internal width.

24. The system of claim 17 further comprising:
a second discharge aperture on the distal end of the elongate housing, the second discharge aperture distinct from the first discharge aperture, and the second aperture fluidly coupled to a second fluid conduit;
a second active electrode of conductive material disposed on the distal end of the elongate housing; and
a second return electrode of conductive material disposed within the second fluid conduit proximate to the second aperture such that at least some fluid flowing in the second fluid conduit contacts the second return electrode before discharging through the second discharge aperture toward the second active electrode.

25. The system of claim 24 further comprising:
the distal end of the elongate housing defines a width and a thickness;
wherein first active electrode further comprises a loop of wire that defines a first outer portion;
wherein second active electrode further comprises a loop of wire that defines a second outer portion; and
the first and second outer portions are aligned along the width such that, when viewed along the thickness, the first and second straight portions overlap.

26. An electrosurgical wand comprising:
an elongate housing that defines a handle end and a distal end;
a connector comprising a first and second electrical pins;
a first discharge aperture on the distal end of the elongate housing, the first discharge aperture fluidly coupled to a first fluid conduit, and the first fluid conduit within the elongate housing;
a first active electrode of conductive material disposed on the distal end of the elongate housing, and the first active electrode electrically coupled to the first electrical pin;
a first return electrode of conductive material disposed within the first fluid conduit proximate to the first discharge aperture, the first return electrode within at least a portion of a fluid path directed to contact the first return electrode before discharging through the first discharge aperture toward the first active electrode, and the first return electrode electrically coupled to the second electrical pin; and
an aspiration aperture on the distal end of the elongate housing fluidly coupled to a second fluid conduit, the second fluid conduit within the elongate housing, wherein the aspiration aperture defines an aperture width, and wherein the second fluid conduit transitions in width from the aperture width to an internal width over a length not less than two times the difference between the aperture width and the internal width.

27. The electrosurgical wand of claim 26 wherein at least a portion of the first active electrode extends over the first discharge aperture.

28. The electrosurgical wand of claim 26 wherein the return electrode is at least one selected from the group consisting of: a coil of wire; and a wire mesh.

29. The electrosurgical wand of claim 26 wherein first active electrode further comprises a loop of wire.

30. The electrosurgical wand of claim 29 wherein the return electrode is a coil of wire that defines a central axis, and wherein the first active electrode defines a straight portion and the central axis is parallel to the straight portion.

31. The electrosurgical wand of claim 26 further comprising:
a first plane defined by the discharge aperture;
a second plane defined by the aspiration aperture; and
wherein the first and second plane are parallel, and the second plane is closer to the handle than the first plane.

32. The electrosurgical wand of claim 26 further comprising:
a second discharge aperture on the distal end of the elongate housing, the second discharge aperture distinct from the first discharge aperture, and the second aperture fluidly coupled to a second fluid conduit;
a second active electrode of conductive material disposed on the distal end of the elongate housing; and
a second return electrode of conductive material disposed within the second fluid conduit proximate to the second aperture such that at least some fluid flowing in the second fluid conduit contacts the second return electrode before discharging through the second discharge aperture toward the second active electrode.

33. The electrosurgical wand of claim 32 further comprising:
the distal end of the elongate housing defines a width and a thickness;
wherein first active electrode further comprises a loop of wire that defines a first outer portion;
wherein second active electrode further comprises a loop of wire that defines a second outer portion; and
the first and second outer portions are aligned along the width such that, when viewed along the thickness, the first and second straight portions overlap.

34. The electrosurgical wand of claim 33 further comprising:
the first outer portion defines a first straight portion;
the second outer portion defines a second straight portion; and
wherein the first and second straight portions are parallel.

35. The electrosurgical wand of claim 26 further comprising:
the first active electrode defines a first exposed surface area; and
the first return electrode defines a second exposed surface area greater than the first exposed surface area.

* * * * *